United States Patent [19]

Clayton et al.

[11] 4,048,320
[45] Sept. 13, 1977

[54] PENICILLINS

[75] Inventors: John Peter Clayton, Horsham; Peter Hubert Bentley, Rudgwick, both of England

[73] Assignee: Beecham Group Limited, England

[21] Appl. No.: 647,131

[22] Filed: Jan. 7, 1976

[30] Foreign Application Priority Data

Jan. 17, 1975 United Kingdom ............... 2021/75
June 17, 1975 United Kingdom ............. 25669/75
Aug. 16, 1975 United Kingdom ............. 34182/75

[51] Int. Cl.$^2$ ................... A61K 31/43; C07D 499/50
[52] U.S. Cl. ................................ 424/271; 260/239.1
[58] Field of Search ................ 260/239.1; 424/271

[56] References Cited

FOREIGN PATENT DOCUMENTS 1,339,007 11/1973 United Kingdom ............ 260/239.1
1,425,571 2/1976 United Kingdom ............ 260/239.1

OTHER PUBLICATIONS

Abstract No. 368, "Program and Abstracts of the 14th Interscience Conference on Antimicrobial Agents and Chemotherapy" Sept. 11-13, 1974, San Francisco, Calif.

*Primary Examiner*—Gerald A. Schwartz
*Attorney, Agent, or Firm*—Jacobs & Jacobs

[57] ABSTRACT

A class of 6-methoxy-α-carboxy penicillins have antibacterial activity against a wide range of Gram-negative organisms.

7 Claims, No Drawings

PENICILLINS

This invention relates to a class of penicillins which have antibacterial activity and are of value in the treatment of infections in animals, including man and poultry, caused by a wide range of Gram-negative organisms. In particular the invention relates to a class of 6-methoxy-α-carboxy penicillins. The invention also relates to a process for the preparation of such compounds, and to pharmaceutical compositions comprising them.

British Patent Specification No. 1,339,007 discloses inter alia a class of 6-substituted acylamino penicillins of general formula (A)

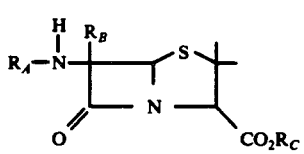
(A)

where $R_A$ represents an acyl group, $R_B$ is a hydroxy or mercapto radical, a substituted or unsubstituted methoxy, ethoxy, methyl, ethyl, methylthio, or ethylthio radical, a carbamoyloxy, carbamoylthio, $C_{1-6}$ alkanoyloxy, $C_{1-6}$ alkanoylthio, cyano or carboxy radical or a derivative of a carboxy radical such as carbamoyl and $R_C$ is a hydrogen atom or a pharmaceutically acceptable esterifying radical or cation.

In abstract No. 368 of the "Program and Abstracts of the 14th Interscience conference on Antimicrobial Agents and Chemotherapy" held on 11th – 13th September, 1974 in San Francisco, Cal., U.S.A., a report is made of a single 6-methoxy penicillin within formula (A) above, namely 6α-methoxy-6β-(2-carboxyphenylacetamido)penicillanic acid.

We have now found a small class of 6-methoxy α-carboxy penicillins which have a high level of antibacterial activity compared to the broad class of compounds disclosed in British Pat. No. 1,339,007 and also compared to the compound 6α-methoxy-6β-(2-carboxyphenylacetamido)penicillanic acid.

According to the present invention there is provided a compound of formula (I):

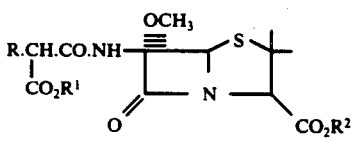
(I)

wherein R is 2- or 3-thienyl, $R^1$ is hydrogen or a pharmaceutically acceptable salting ion, and $R^2$ is hydrogen, or a pharmaceutically acceptable salting ion or in vivo hydrolysable ester radical.

Suitable salting ions for the groups $R^1$ and $R^2$ include metal ions e.g. aluminium, alkali metal ions such as sodium or potassium, alkaline earth metal ions such as calcium or magnesium, and ammonium or substituted ammonium ions for example those from lower alkylamines, such as triethylamine, hydroxy-lower alkylamines such as 2-hydroxyethylamine, bis-(2-hydroxyethyl)-amine or tri-(2-hydroxyethyl)-amine, cycloalkylamines such as bicyclohexylamine, or from procaine, dibenzylamine, N,N-dibenzylethylenediamine, 1-ephenamine, N-ethylpiperidine, N-benzyl-β-phenethylamine, dehydroabietylamine, N,N'-bis-dehydroabietylethylenediamine, or bases of the pyridine type such as pyridine, collidine or quinoline, or other amines which have been used to form salts with benzylpenicillin.

In vivo hydrolysable pharmaceutically acceptable ester radicals for the group $R^2$ are those which hydrolyse in the human body to produce the parent acid. Suitable examples include acyloxyalkyl groups such as acetoxymethyl, pivaloyloxymethyl, α-acetoxyethyl, α-acetoxybenzyl and α-pivaloyloxyethyl groups; alkoxycarbonyloxyalkyl groups, such as ethoxycarbonyloxymethyl and α-ethoxycarbonyloxyethyl; and lactone, thiolactone and dithiolactone groups, i.e. ester groups of formula:

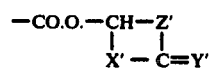

wherein X' and Y' are oxygen or sulphur and Z' is an ethylene group or a 1,2-phenylene group optionally substituted by lower-alkoxy, halogen or nitro. δ

Preferred ester groups are the phthalide and 5,6-dimethoxyphthalide esters.

Specific compounds within this invention include the following:
- 6-β-(2-carboxy-2-thien-3'-ylacetamido)-6-α-methoxypenicillanic acid;
- 6-β-(2-carboxy-2-thien-2'-ylacetamido)-6-α-methoxypenicillanic acid.

The compounds of formula (I) may be prepared by reacting a compound of formula (III) or an N-silyl or N-phosphorylated derivative thereof:

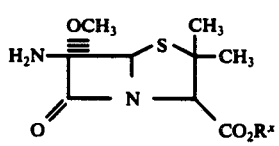
(III)

wherein $R^x$ is hydrogen or a carboxyl blocking group; with an N-acylating derivative of an acid of formula (IV):

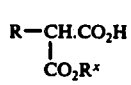
(IV)

wherein R is as defined with respect to formula (I) above; and thereafter if necessary carrying out one or more of the following steps:
i. removal of any silyl or phosphoryl groups by hydrolysis or alcoholysis;
ii. removal of any carboxyl blocking groups;
iii. converting the product to a salt or ester thereof.

By the term "N-silyl derivative" of compound (III), we mean the product of reaction of the 6-amino group of compound (III) with a silylating agent such as a halosilane or a silazane of the formula:

$L_3$ Si U; $L_2$ Si $U_2$; $L_3$ Si $NL_2$;
$L_3$ Si NH Si $L_3$; $L_3$ Si.NH.COL; $L_3$ Si. NH.CO.NH.Si $L_3$;
L NH.CO.NH.Si $L_3$; LC.OSi $L_3$
$|$
$NSiL_3$ wherein U is a halogen and the various groups L which may be the same or different, each represents hydrogen or alkyl, alkoxy, aryl, or aralkyl. Preferred silylating agents are silyl chlorides, particularly trimethylchlorosilane.

The term "N-phosphorylated" derivative of compound (III) is intended to include compounds wherein the 6-amino group of formula (III) is substituted with a group of formula:

$- P.R_a R_b$ wherein $R_a$ is an alkyl, haloalkyl, aryl, aralkyl, alkoxy, haloalkoxy, aryloxy, aralkyloxy or dialkylamino group, $R_b$ is the same as $R_a$ or is halogen or $R_a$ and $R_b$ together form a ring.

Suitable carboxyl-blocking derivatives for the group $—CO_2R^x$ in formulas (III) and (IV) include salts, esters, and anhydride derivatives of the carboxylic acid. The derivative is preferably one which may be readily cleaved at a later stage of the reaction. Suitable salts include tertiary amine salts, such as those with tri-loweralkylamines. N-ethyl-piperidine, 2,6-lutidine, pyridine, N-methylpyrrolidine, dimethylpiperazine. A preferred salt is with triethylamine.

Suitable ester groups of formula $CO_2R^x$ include the following:

i. $—COOCR_cR_dR_e$ wherein at least one of $R_c$, $R_d$ and $R_e$ is an electron-donor e.g. p-methoxyphenyl, 2,4,6-trimethylphenyl, 9-anthryl, methoxy, acetoxy, methoxymethyl, benzyl or fur-2-yl. The remaining $R_c$, $R_d$ and $R_e$ groups may be hydrogen or organic substituting groups. Suitable ester groups of this type include p-methoxybenzyloxycarbonyl, 2,4,6-trimethylbenzyloxy carbonyl, bis-(p-methoxyphenyl)methoxycarbonyl, 3,5-di-t-butyl-4-hydroxybenzyloxycarbonyl, methoxymethoxycarbonyl and benzyloxycarbonyl.

ii. $—COOCR_cR_dR_e$ wherein at least one of $R_c$, $R_d$ and $R_e$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R_c$, $R_d$ and $R_e$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

iii. $—COOCR_cR_dR_e$ wherein at least two of $R_c$, $R_d$ and $R_e$ are hydrocarbon such as alkyl e.g. methyl or ethyl, aryl e.g. phenyl and the remaining $R_c$, $R_d$ and $R_e$ group, if there is one, is hydrogen. Suitable esters of this type include t-butyloxycarbonyl, t-amyloxycarbonyl, diphenylmethoxycarbonyl and triphenylmethoxycarbonyl.

iv. $—COOR_f$ wherein $R_f$ is adamantyl, phenyl, alkyl-substituted phenyl, 2-benzyloxyphenyl, 4-methylthiophenyl, tetrahydrofur-2-yl, tetrahydropyran-2-yl, pentachlorophenyl;

v. Silyloxycarbonyl groups obtained by reaction of a silylating agent as described above with the carboxylic acid group;

vi. $CO_2P.R_aR_b$, wherein $R_a$ and $R_b$ are as defined above;

vii. An in vivo hydrolysable ester radical, such as defined above.

The carboxyl group may be regenerated from any of the above esters by usual methods for example, acid — the base — catalysed hydrolysis, or by enzymically — catalysed hydrolysis.

Alternative methods of cleavage include:
reaction with Lewis acids, such as trifluoroacetic acid, formic acid, hydrochloric acid in acetic acid, zinc bromide in benzene and aqueous solutions or suspensions of mercuric compounds. (The reaction with the Lewis acid may be facilitated by addition of a nucleophile such as anisole);

reduction with agents such as zinc/acetic acid, zinc/formic acid, zinc/lower alcohol, zinc/pyridine, palladised-charcoal and hydrogen, and sodium and liquid ammonia;

attack by nucleophiles, such as those containing a nucleophilic oxygen or sulphur atom for example alcohols, mercaptans and water; oxidative methods, for example, those which involve the use of hydrogen peroxide and acetic acid; and irradiation.

A reactive N-acylating derivative of the acid (IV) is employed in the above process. The choice of reactive derivative will of course be influenced by the chemical nature of the substituents of the acid.

Suitable N-acylating derivatives include an acid halide, preferably the acid chloride or bromide. Acylation with an acid halide may be effected in the presence of an acid binding agent for example tertiary amine (such as triethylamine or dimethylaniline), an inorganic base (such as calcium carbonate or sodium bicarbonate) or an oxirane, which binds hydrogen halide liberated in the acylation reaction. The oxirane is preferably a $(C_{2-6})$-1,2-alkylene oxide - such as ethylene oxide or propylene oxide. The acylation reaction using an acid halide may be carried out at a temperature in the range $-50°$ to $+50°C$, preferably $-20°$ to $+30+C$, in aqueous or non-aqueous media such as aqueous acetone, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (IV) or a salt thereof with a halogenating (e.g. chlorinating or brominating) agent such as phosphorus pentachloride, thionyl chloride or oxalyl chloride.

Alternatively, the N-acylating derivative of the acid (IV) may be a symmetrical or mixed anhydride. Suitable mixed anhydrides are alkoxyformic anhydrides, or anhydrides with, for example carbonic acid monoesters, trimethyl acetic acid, thioacetic acid, diphenylacetic acid, benzoic acid, phosphorus acids (such as phosphoric or phosphor acids), sulphuric acid or aliphatic or aromatic sulphonic acids (such as p-toluenesulphonic acid). The mixed or symmetrical anhydrides may be generated in situ. For example, a mixed anhydride may be generated using N-ethoxycarbonyl-2-ethoxy-1,2-dihydroquinoline. When a symmetrical anhydride is employed, the reaction may be carried out in the presence of 2,4-lutidine as catalyst.

Alternative N-acylating derivatives of acid (IV) are the acid azide, or activated esters such as esters with cyanomethanol, p-nitrophenol, 2,4-dinitrophenol, thiophenol, halophenol, including pentachlorophenol, monomethoxyphenol or 8-hydroxyquinoline; or amides such as N-acylsaccharins or N-acylphthalimides; or an alkylidene iminoester prepared by reaction of the acid (IV) with an oxime; or the ketene acid chloride of the malonic acid (IV), which gives the α-carboxy compound directly.

Some activated esters, for example the ester formed with 1-hydroxybenztriazole or N-hydroxysuccinimide, may be prepared in situ by the reaction of the acid with the appropriate hydroxy compound in the presence of a carbodimide, preferably dicyclohexylcarbodiimide.

Other reactive N-acylating derivatives of the acid (IV) include the reactive intermediate formed by reaction in situ with a condensing agent such as a carbodiimide, for example N,N-diethyl-, dipropyl- or diisopropyl-carbodiimide, N,N'-dicyclohexylcarbodiimide, or N-ethyl-N'-γ-dimethylaminopropylcarbodiimide; a suitable carbonyl compound, for example N,N'carbonyldiimidazole or N,N'-carbonylditriazole; an isoxazolinium salt, for example N-ethyl-5-phenylisoxazolinium-3- sulphonate or N-t-butyl-5-methylisoxazolinium perchlorate; or an N-alkoxycarbonyl-2-alkoxy-1,2-dihydroquinoline, such as N-ethoxycarbonyl-2-ethoxy-1,2-dihydroquinoline. Other condensing agents include Lewis acids (for example $BBr_3 - C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan, or tetrahydrofuran.

The compounds (III) may be prepared for example by the method described by Jen et al (J.Org. Chem. 1973, 38, 2857) from an ester of a compound of formula:

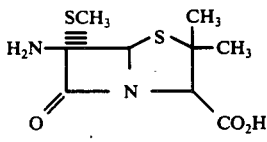

which compound may in turn be prepared from the corresponding 6-isocyano compound as described in our W. German Offenlegungsschrift No. 2,407,000.

Compounds of formula (I) may also be prepared by reacting a compound of formula (VI):

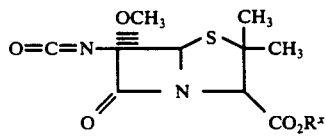

wherein $R^x$ is as defined above with respect to formula (III) above; with an acid of formula (IV) or a carbanion of formula (VIA) $R-CH-CO_2R^x$; and thereafter if necessary carrying out one or more of the following steps:
 i. removal of any carboxyl blocking group;
 ii. converting the product to a salt or ester thereof.

This reaction is preferably carried out at a temperature in the range − 10° to + 50° C in an inert organic solvent, such as methylene dichloride, in the presence of a basic catalyst such as triethylamine, pyridine or a nitrogen-containing aromatic mono- or bi-cyclic compound such as 4-methoxy(dimethylamino)pyridine, 1-methyl(benz)imidazole or imidazo [1,2-a]pyridine.

A third method of preparation of the compounds of formula (I) comprises:

a. protecting the 3-carboxylic acid group of a 6-α-methoxy-6-β-acylaminopenicillanic acid with a carboxyl blocking group.
b. reacting the protected penicillanic acid to form an imino bond on the 6-amido nitrogen atom;
c. reacting the resulting compound to introduce a group $QR_f$ on the imino carbon atom, wherein Q is oxygen, sulphur or nitrogen and $R_f$ is an alkyl group of form 1 to 12 carbon atoms or an aralkyl group of from 7 to 14 carbon atoms, to form an iminoether, iminothioether or amidine (when Q is O, S or N, respectively);
d. reacting with an acylating derivative of an acid of formula (IV) above;
e. treating with water or an alcohol; and
f. thereafter if necessary carrying out one or more of the following steps:
 i. removal of any carboxyl blocking groups;
 ii. converting the product to a salt or ester thereof.

In the above process, after protection of the 3-carboxylic acid group, the protected penicillanic acid is reacted with an agent to form an imino bond on the 6-amino nitrogen atom. Preferably an imino halide is formed of formula (VII):

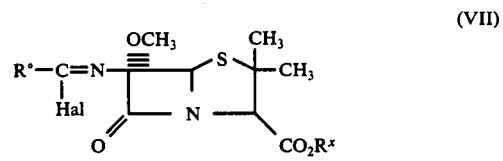

wherein $R^o$ is the residue of an organic acylamino sidechain of a penicillin, $R^x$ is a carboxyl blocking group and Hal represents a halogen atom. A suitable agent for preparing an imino halide is an acid halide in the presence of an acid binding agent such as a tertiary amine, e.g. pyridine, triethylamine, or N,N,-dimethylaniline. Examples of suitable acid halides are phosphorus pentachloride, phosgene, phosphorus pentabromide, phosphorus oxychloride, oxalyl chloride and p-toluene sulphonic acid chloride. Phosphorus pentachloride and phosphorus oxychloride are preferred. The reaction may be conducted under cooling, preferably at temperatures from 0° C to −30° C when phosphorus pentachloride is employed. The amount of the tertiary amine is preferably 3-5 mols per mol of phosphorus pentachloride. It is also preferable to use the phosphorus halide in an amount slightly in excess of that of the starting material.

The resulting imino compounds are then treated to introduce a—$QR_f$ grouping, onto the imino carbon atom, to produce a compound of formula (VIII):

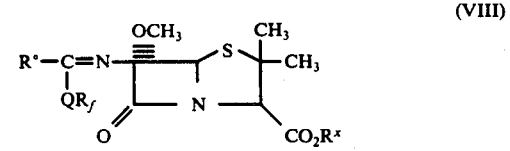

wherein $R^o$, Q, $R_f$ and $R^x$ are as defined above.

This is preferably effected by reacting an imino halide with corresponding alcohol. Examples of suitable alcohols for reaction with the imino halide are aliphatic alcohols containing from 1 to 12 carbon atoms, preferably 1 to 5 carbon atoms, such as methanol, ethanol, propanol, isopropyl alcohol, amyl alcohol and butyl alcohol, and aralkyl alcohols such as benzyl alcohol and 2-phenyl-ethanol-1. The reaction of the alcohol with the imino halide is preferably effected in the presence of an acid binding agent, such as a tertiary amine, preferably pyridine, and the reaction is usually carried out without isolating the imino halide from the reaction mixture.

Thereafter the compound (VIII) is caused to react with an N-acylating derivative of an acid of formul (IV). The comments made above concerning such N-acylating derivative, and the conditions for carrying out acylations also apply in this case. In particular the presence of a tertiary amine such as pyridine or N,N-dimethylaniline in the reaction system is preferred. The product from such an acylation has formula (IX):

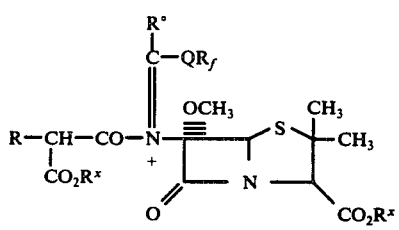

(IX)

Finally, the addition compound (IX) is treated with water or alcohol. The water treatment may be conducted together with the isolation of the desired material. That is, water or a saturated aqueous solution of sodium chloride is added to the compound (IX) and then the aqueous layer formed is separated from the organic solvent layer.

Alternatively a compound of formula (IX A):

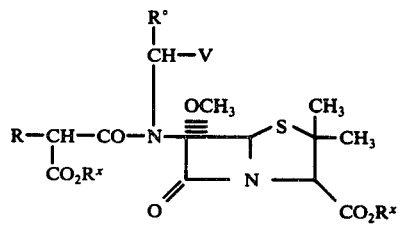

(IXA)

wherein R, R°, and $R^x$ are as defined above and V is the residue of an N-acylating derivative of the acid (IV), (e.g. hydroxy, halogen, acyloxy, aryloxy, amino, cyano, azido);may be prepared by reaction of the corresponding N-acylating derivative of (IV) with the Schiff's base formed by reacting 6-α-methoxy-6-β-aminopenicillanic acid (or a carboxyl protected derivative thereof) with an aldehyde R°.CHO. The compound (IXA) may be hydrolysed to a compound (I) with water optionally in the presence of acid or base.

A further method for the preparation of compounds of formula (I) is by hydrolysis of an N-acylbenzyl-6-α-methoxy-penicillan of formula (X):

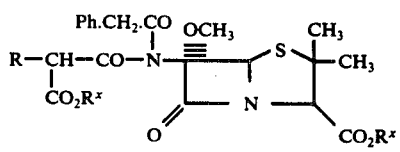

(X)

wherein R, and $R^x$ are as defined above. The hydrolysis may be an acid- or base-catalysed chemical hydrolysis or may be an enzymic hydrolysis with the aid of penicillin acylase. The compound (X) may be prepared either from an imino-halid compound of formula (VII) above by reaction with a salt of the acid (IV); or by the action of an acid halide of the acid (IV) with a 6-N-alkali metal derivative of benzyl 6α-methoxypenicillin or alternatively with its 6N-trimethylsilyl derivative.

A further method for the preparation of compounds of formula (I) comprises reacting a compound of formula (XIII):

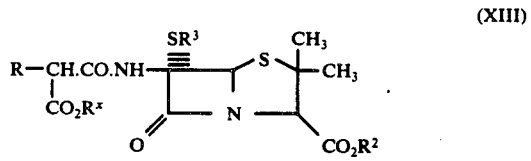

(XIII)

wherein R, and $R^2$ are as defined with respect to formula (I) and $R^3$ is lower alkyl or benzyl:
A. with chlorine or bromine at −25° to 80° C and subsequently decomposing the resultant halosulphonium halide with methanol and a base; or
B. with methanol in the presence of a metal ion such as a tellurium (III), lead (IV), bismuth (V) mercury, lead, cadmium or thallium salts and subsequently removing the carboxyl protecting group.

Preferably the reaction is carried out at −50° to +25° C in a solvent.

Compounds (I) may also be prepared by reducing a compound of a formula (XV):

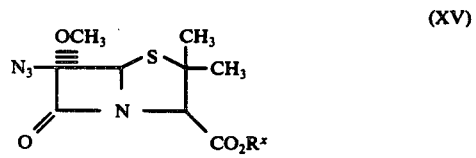

(XV)

wherein $R^x$ is as defined above; and simultaneously or subsequently acylating with an N-acylating derivative of an acid of formula (IV) above and thereafter if necessary:
i. removing any carboxyl blocking group; converting the product to a salt or ester thereof. Suitable N-acylating derivatives of the acid (IV) are as described above.

Various methods of carrying out the reduction of the azido group may be used, but a preferred method is by catalytic hydrogenation using a noble metal catalyst such as platinum, palladium or oxides thereof.

The intermediate of formula (XV) may be prepared as described in British Pat. No. 1,339,007.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) together with a pharmaceutical carrier or excipient.

The compositions may be formulated for administration by any route, although an oral administration is preferred. The compositions may be in the form of tablets, capsules, powders, granules, lozenges, or liquid preparations, such as oral or sterile parenteral solutions or suspensions.

Tablets and capsules for oral administration may be in unit dose presentation form, and may contain conventional excipients such as binding agents, for example syrup, acacia, gelatin, sorbitol, tragacanth, or polyvinyl pyrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups, or elixirs, or may be presented as dry product for reconstitution with water or other suitable vehicle before use. Such liquid preparations may contain conventional additives such as suspending agents, for example sorbitol, syrup, methyl cellulose, glucose syrup, gelatin, hydroxyethylcellulose, carboxymethyl cellulose, alluminum stearate gel or hydrogenated edible fats, emulsifying agents, for example lecithin, sorbitan monooleate, or acacia; non-aqueous vehicles (which may include edible oils), for example almond oil, fractionated coconut oil oily esters such as glycerine, propylene glycol, or ethyl alcohol; preservatives, for example methyl or propyl p-hydroxybenzoate or sorbic acid, and if desired conventional flavouring or colouring agents.

Suppositories will contain conventional suppository bases, e.g. cocoa, butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplid to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% ot 99% by weight, preferably from 10–60% by weight, of the active material, depending on the method of administration. Where the compositions comprise dosage units, each unit will preferably contain from 50–500 mg. of the active ingredient. The dosage as employed for adult human treatment will preferably range from 100 to 3000 mg. per day, for instance 1500 mg. per day, depending on the route and frequency of administration.

It will be clear that the side-chain of the penicillins of formula (I) contains a potentially asymmetric carbon atom. This invention includes all the possible epimers of compounds (I) as well as mixtures of them.

The compounds of this invention have an unusual stability to Gram-negative $\beta$-lactamases and are active against all the important Gram-negative pathogens with the exception of Pseudomonas aeraginosa.

The following Examples illustrate the preparation of some of the compounds of this invention.

EXAMPLE 1 a. Benzyl 6α-methoxy, 6β-aminopenicillanate

The corresponding 6α-methylthio derivative (see West German Offenlegungsschrift No. 2,407,000) was converted into the title compound according to Jen et. al. (J. Org. Chem. 1973, 38, 1857).

b. Benzyl 6α-methoxy, 6β-(2'-phenoxycarbonylthien-3-yl-acetamido)penicillanate A solution of benzyl 6α-methoxy, 6β-aminopenicillanate (1.6 mmole) in alcohol-free methylene chloride (15 ml) and pyridine (0.2 ml) was treated at 0°–5° with a solution of the acid chloride prepared from phenyl hydrogen thien-3-ylmalonate (2 mmole) in methylene chloride (4 ml). After 2.5 hours, the solution was washed with water, dilute hydrochloric acid, water, dilute sodium bicarbonate dried and evaporated. Chromatography on silica gel provides the desired di-ester in 52.2% yield. N.m.r. (CDCl$_3$) $\delta$ = 1.35 (6H, s, gem dimethyls), 3.55 (3H, s, OC$\underline{H}_3$) 4.25 (1H, s, C$_3$ proton), 5.09 (1H, s, 2'-proton), 5.27 (2H, s, OC$\underline{H}_2$Ph), 5.69 (1H, s, C$_5$ proton), 7.09 – 7.88 (13H, m, phenyl and thienyl protons).

c. 6α-Methoxy,6β-(2'-phenoxycarbonylthien-3-ylacetamido) penicillanic acid

A solution of the di-ester from (b) (150 mg) in absolute ethanol (10 ml), water (3 ml) and N-sodium bicarbonate (1 equiv) was treated with 10% Pd/C (200 mg) over 2.5 hours, at 50 p.s.i. Freeze drying provided the title compound as its sodium salt in 62% yield. N.m.r. (D$_2$O) $\delta$ = 1.4 and 1.6 (6H, 2s, gem dimethyls), 3.45 and 3.60 (3H, 2s, OCH$_3$) 4.35 (1H, s, C$_3$ proton), 5.1 (1H, s, 2'proton), 5.6 (1H, s, C$_5$ proton), 7–7.7 (8H, m, phenyl and thienyl protons).

d. 6-β- (D,L-2-Carboxy-2-thien-3'-ylacetamido)-6-α-methoxypenicillanic acid

Sodium 6-α-methoxy-6-β-(D,L-2-phenoxycarbonyl-2-thien-3'ylacetamido)penicillanate (0.460, 0.9 mmole) and sodium tetraborate decahydrate (0.7 g) in water (15 ml) were stirred at R.T. for 4 hours. The solution was then acidified to pH 4.0, washed with ethyl acetate (2 × 10 ml), acidified to pH 1.5 and extracted with ethyl acetate (2 × 20 ml). The extracts were washed with water then extracted with dilute sodium bicarbonate to pH 6.5. This aqueous extract was washed with ether and freeze dried to give the disodium salt of the title compound, 0.240 g. 58.2%; t.l.c. (SiO$_2$: chloroform/acetone/acetic acid; 7:7:1) Rf = 0.25; n.m.r. (D$_2$O), $\delta$ = 1.55 (6H, s, gem dimethyls), 3.65, 3.75, (3H, 2 × s, —OCH$_3$), 4.5 (1H, s, C$_3$ proton), 5.7 (1H, s, C$_5$ proton), 7.2 — 7.8 (3H, m, thienyl protons).

EXAMPLE 2 a. Benzyl 6α-methoxy, 6β-(2'-benzyloxycarbonyl-thien-3-ylacetamido)penicillanate A solution of benzyl 6α-methoxy, 6β-aminopenicillanate (1.6 mmole) in alcohol-free methylene chloride (15 mls) and pyridine (0.2 ml) was treated at 0°–5° with the acid chloride of monobenzyl 3-thienylmalonate (2 mmole) dissolved in methylene chloride (4 ml). After 2.5 hours, the reaction was worked up as above. Chromatography on silica gel gave the pure desired diester (0.64 g., 66%) as a froth. $\gamma_{max}^{CHCl_3}$ 3 3250, 1770, 1735, 1685, 1495 cm.$^{-1}$ $\delta$(CDCl$_3$) 1.33 (bs, 6H, C2-C$\underline{H}_3$), 3,43 and 3,47 (2s, 3H, OC$\underline{H}_3$), 4.50 (2s, 1H, C2'-H), 4.85 (s, 1H, C3-H), 5.28 (2s, 4H, CH$_2$O), 5.63 (s, 1H, C5-H), 7.5 (m, 8H, Ar-H), 7.74 and 7.91 (2bs, 1H in all, N$\underline{H}$).

b. 6α-methoxy, 6β-2'-carboxy-thien-3-ylacetamidopenicillanic acid

A solution of the dibenzyl ester (200 mg) from 1(a), in absolute ethanol (10 ml) water (3 ml) and N-sodium bicarbonate (0.5 ml) was treated with 10% Pd/C (200 mg) over 4 hours at N.T.P. After filtration and evaporation the product was partitioned between ethyl acetate and water at pH 2. The ethyl acetate phase on drying gave the title compound which was converted to its disodium salt by dissolving in aqueous ethanol and adjusting the pH to 6.5 and freeze drying.

The product (140 mgs) was essentially pure by TLC. KBr 1760, 1670, 1605, 1500, 1365cm$^{-1}$; δ(D$_2$O) 1.4 (bs, 6H, C$\underline{H}_3$) 3.45 and 3.52 (2s, 3H, OC$\underline{H}_3$), 4.26 (s, 1H, C3-H), 5.52 (s, 1H, C5-H) and 7.1 - 7.6 (m, 3H, Ar-H). C2'-H signal obscured by HOD.

EXAMPLE 3 a. Benzyl 6,β-(D,L-2-benzyloxycarbonyl-2-thien-3'-ylacetamido)-6,α-methylthio penicillanate Benzyl-6-β-amino-6-α-methylthio penicillanate toluene-4-sulphonate (1.57g., 3.0 mmole) (see W. German OLS No. 2,407,000) was shaken with ethyl acetate (100 ml) and 0.5N sodium bicarbonate solution (75 ml) at 0°-5° until all had dissolved. The ethyl acetate layer was separated, the aqueous layer extracted with ethyl acetate (2 × 25 ml) and the combined extracts dried (MgSO$_4$) and evaporated to give benzyl 6-β-methylthiopenicillanate. This was dissolved in dichloromethane (60 ml) containing pyridine (0.67 ml), cooled in an ice bath and treated with 2-benzyloxycarbonyl-2-thien-3'-ylacetyl chloride (prepared from benzyl hydrogen thien-3-ylmalonate, 5.0 mmole), in dichloromethane (20 ml). The solution was stirred for two hours then evaporated to give an oil which was dissolved in ethyl acetate, washed with water, 10% citric acid solution, water, N sodium bicarbonate solution and saturated brine, then dried and evaporated to give an oil. Chromatography on silica gel provided the title product, 65% yield; γmax (CHCl$_3$), 3300, 1780, 1740, 1685, 1495cm$^{-1}$; n.m.r. (CDCl$_3$), δ = 7.79, 7.69 (1H, 2 × s, —NHCO—), 7.6 (13H, m, aromatic and thienyl protons), 5.61 (1H, s, C$_5$ proton), 5.27 (4H, 2 × s, 2 × -CO$_2$C$\underline{H}_2$Ph), 4.73

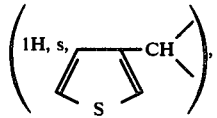

4.51, 4.48 (1H, 2 × s, C$_3$proton), 2.19, 2.27 (3H, 2 × s, —SCH$_3$), 1.39, 1.34 (6H, 2 × s gem dimethyls).

b. Benzyl 6-β-(D,L-2-benzyloxycarbonyl-2-thien-3'-ylacetamido)-6-α-methoxypenicillanate Benzyl 6-β-(D,L-2-benzyloxycarbonyl-2-thein-3'-ylacetamido)-6-α-methylthiopenicillanate (0.25 g. 0.41 mmole) was dissolved in anhydrous methanol (2.5 ml) and d.m.f. (2.5 ml) then silver nitrate (0.123 g) in methanol (0.8 ml) and d.m.f. (0.8 ml) was added. The solution was stirred at 0°-5° for 2 hours, diluted with ether (20 ml), filtered and the filtrate diluted with ether (60 ml) and ethyl acetate (20 ml) washed with water (4 × 50 ml), dried and evaporated to give a gum. Chromatography on silica gel gave the title compound 0.155 g, 63.8%; t.l.c. (SiO$_2$; ethyl acetate/60°-80° petrol; 3:7) Rf = 0.23; n.m.r. (CDCl$_3$), δ — 8.2 - 7.0 (13H, m, aromatic and thienyl protons), 5.65 (1H, s, C$_5$proton), 5.28 (4H, s, 2 × -CO$_2$C$\underline{H}_2$Ph),

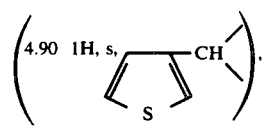

4.48 (1H, s, C$_3$ proton) 3.43 (3H, s, —OCH$_3$), 1.30 (6H, s, gem dimethyls).

c. Hydrogenolysis as in Example 1(b) produced 6-α-methoxy-6β-2-carboxy-thien-3-ylacetamido penicillanic acid.

EXAMPLE 4

6, '-Methoxy-6,β-(D,L-2-thien-2'-ylacetamido)-penicillanic acid

Sodium 6,α-methoxy-6,β-(D,L-2-phenoxycarbonyl-2-thien-2'-ylacetamido)penicillinate *(0.65 g), and sodium tetraborate decahydrate (1.0g) in water (50 ml) were stirred for 2.5 hours at room temperature. The solution was then acidified to pH 4.0 and washed with ethyl acetate (3 × 50 ml), acidified to pH 2.0 and extracted with ethyl acetate (2 × 50 ml), dried over anhydrous Mg SO$_4$ and evaporated in vacuo to yield 0.49 g (93%) of a straw coloured foam, t.l.c. (SiO$_2$; chloroform/ acetone/acetic acid, 50:50:7) Rf = 0.21; N.M.R. [(CD$_3$)$_2$CO], * See out co-pending application Ser. No. 647,176 of even date δ = 1.50 (6H, m,gem dimethyls), 3.52 (3H, d, —OC$\underline{H}_3$), 4.50 (1H, d, 3-H), 5.32 (1H, s, <C$\underline{H}$CONH-), 5.65 (1H, s, 5-H), 7.3 (3H, m, thienyl aromatics) 8.88 (1H, d, —CON$\underline{H}$—), 9.28 (2H, s, —CO$_2$H).

BIOLOGICAL DATA Comparison with 6α-methoxy-6β-(2-carboxyphenylacetamido) penicillanic acid The results of a microbiological evaluation of 6α-methoxy-6β-(2-carboxyphenylacetamido)penicillanic acid [6-methoxy carbenicillin] and 6-α-methoxy-6β(2-carboxythien-3'-ylacetamido)penicillanic acid [6-methoxy ticarcillin] are given in table I, which shows MIC values (serial dilution in nutrient agar) for the two compounds against a range of Gram-negative bacteria and Strep. Faecalis.

It can be seen from the table I that the 3-thienyl compound (6-methoxy ticarcillin) was consistently two-fold more active than the corresponding phenyl compound (6-methoxy carbenicillin).

Table I

| Organism | | MIC* (μg/ml) 6-methoxy carbenicillin | 6-methoxy ticarcillin |
|---|---|---|---|
| E. coli | JT1 | 5.0 | 2.5 |
| | JT103 | 5.0 | 2.5 |
| | JT147 | 12.5 | 5.0 |
| | JT2OR+ | 5.0 | 5.0 |
| | JT39R+ | 12.5 | 5.0 |
| | JT56R+ | 12.5 | 5.0 |
| | JT68R+ | 12.5 | 5.0 |
| | JT454C+ | 5.0 | 5.0 |
| | JT460C+ | 12.5 | 5.0 |
| Klebsiella aerogenes | I229 | 12.5 | 5.0 |
| | T312 | 12.5 | 5.0 |
| | I281 | 12.5 | 5.0 |
| | E70 | 5.0 | 2.5 |
| | B195R+ | 25 | 5.0 |
| Serratia marcescens | US1 | 5.0 | 2.5 |
| | US30 | 12.5 | 5.0 |
| | US39R+ | 5.0 | 2.5 |

Table I-continued

MIC* (μg/ml)

| Organism | | 6-methoxy carbenicillin | 6-methoxy ticarcillin |
|---|---|---|---|
| Citrobacter | W18 | 12.5 | 2.5 |
| freundii | T745 | 5.0 | 2.5 |
| Enterobacter | T755 | 5.0 | 2.5 |
| aerogenes | T730 | 5.0 | 1.2 |
| E. cloacae | T629 | 5.0 | 2.5 |
|  | T763 | 5.0 | 1.2 |
| Proteus | H-WF | 5.0 | 2.5 |
| mirabilis | BS66 | 5.0 | 2.5 |
|  | CT13 | 5.0 | 2.5 |
|  | T251 | 5.0 | 2.5 |
| P. morganii | DU10 | 5.0 | 2.5 |
|  | DU718 | 5.0 | 2.5 |
| P. vulgaris | C | <0.5 | <0.5 |
|  | I | 5.0 | 2.5 |
|  | K | 12.5 | 5.0 |
| P. rettgeri | R110 | 5.0 | 2.5 |
|  | B | 5.0 | 2.5 |
|  | I | 5.0 | 5.0 |
| Streptococcus | Weaver | >500 | >500 |
| faecalis | Page | >500 | >500 |
|  | A | >500 | >500 |

We claim:

1. A compound of formula (I):

(I)

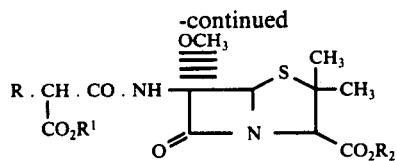

where R is 2- or 3- thienyl and R¹ is hydrogen or a pharmaceutically acceptable salting ion and R² is hydrogen, or a pharmaceutically acceptable salting ion or conventional pharmaceutically acceptable hydrolysable ester radical.

2. A compound as claimed in claim 1 where R is 3-thienyl.

3. A compound as claimed in claim 1 where is 6-β-(2-carboxy-2-thien-3'-ylacetamido)-6-α-methoxy penicillanic acid.

4. A compound as claimed in claim 1 which is 6-β-(2-carboxy-2-thien-2'-ylacetamido)-6-α-methoxy-penicillanic acid.

5. A pharmaceutical composition having antibacterial activity comprising an antibacterially effective amount of a compound as claimed in claim 1 together with a pharmaceutical carrier or excipient.

6. A pharmaceutical composition according to claim 5 in which the compound is 6-β-(2-carboxy-2-thien-3'-ylacetamido)-6-α-methoxy penicillanic acid.

7. A pharmaceutical composition according to claim 5 in which the compound is 6-β-(2-carboxy-2-thien-2'-ylacetamido)-6-α-methoxy penicillanic acid.

* * * * *